(12) United States Patent
Palmer et al.

(10) Patent No.: US 8,168,829 B2
(45) Date of Patent: May 1, 2012

(54) SYNTHESIS OF QUATERNARY SALT COMPOUNDS

(75) Inventors: David C. Palmer, Doylestown, PA (US); Sergio Casco-Cancian, Bethlehem, PA (US); Tong Xiao, Edison, NJ (US); Kirk L. Sorgi, Doylestown, PA (US); Armin Roessler, Tengen (DE); Anita Vladislavic, Schaffhausen (CH); Roger Faessler, Stetten SH (CH)

(73) Assignee: Janssen Pharmaceutica N.V., Beerse (BE)

( * ) Notice: Subject to any disclaimer, the term of this patent is extended or adjusted under 35 U.S.C. 154(b) by 532 days.

(21) Appl. No.: 12/256,114

(22) Filed: Oct. 22, 2008

(65) Prior Publication Data

US 2009/0112004 A1   Apr. 30, 2009

Related U.S. Application Data

(60) Provisional application No. 60/982,802, filed on Oct. 26, 2007.

(51) Int. Cl.
*C07C 211/00* (2006.01)
(52) U.S. Cl. ..................................................... 564/306
(58) Field of Classification Search .................... 564/306
See application file for complete search history.

(56) References Cited

U.S. PATENT DOCUMENTS

| 4,450,174 A | 5/1984 | Green et al. |
| 4,845,289 A | 7/1989 | Ries et al. |
| 6,172,061 B1 | 1/2001 | Nishimura et al. |
| 6,268,354 B1 | 7/2001 | Nishimura et al. |
| 6,444,846 B1 | 9/2002 | Smith et al. |
| 2006/0029337 A1 | 2/2006 | Vancoille et al. |
| 2006/0293379 A1 | 12/2006 | Lagu et al. |
| 2009/0112003 A1 | 4/2009 | Li |

FOREIGN PATENT DOCUMENTS

| CN | 1680278 A | 10/2005 |
| EP | 288857 A | 11/1988 |
| WO | WO 00/10965 A | 3/2000 |

OTHER PUBLICATIONS

Bolt, "Mechanisms of Carcinogenicity of Methyl Halides", *Critical Reviews in Toxicology*, 1993, 23(3), 237-253.
Hashimoto et al., "Process Development of 4-[N-Methyl-N-)tetrahydropyran-4-yl)aminomethyl]aniline Dehydrochloride: A Key Intermediate for TAK-779 a Small-Molecule Nonpeptide CCR5 Antagonist", *Organic Process Research and Development*, 2002, 6, 70-73.
Ikemoto et al., "Development of a New Synthetic Route of a Non-Peptide CCR5 Antagonist, TAK-779, for Large Scale Preparation", *Organic Process Research and Development*, 2000, 4, 520-525 (XP002513618).
Ikemoto et al., "Practical Synthesis of an Orally Active CCR5 Antagonist, 7-{4-[2-(butoxy)-ethoxy-phenyl]-N-(4-{methyl-(tetrahydro-2H-pyran-4-yl)amino}methyl]phenyl)-1-propyl-2,3-dihydro-1H-1-benzazepine-4-carboxamide", *Organic Process Research and Development*, 2005, 9, 168-173).
Ikemoto et al., "Convenient, Efficient Synthesis of TAK-779, a Non-Peptide CCR5 Antagonist: Development of Preparation of Various Ammonium Salts using Trialkylphosphite and N-Halogenosuccinimide", *Tetrahedron*, 2001, 57, 1525-1529.
Shiraishi et al., "Discovery of Novel, Potent, and Selective Small-Molecule CCR5 Antagonists as Anti-HIV Agents: Synthesis and Biological Evaluation of Anilide Derivatives with a Quaternary Ammonium Moiety", *J.Med.Chem.*, 2000, 43, 2049-2063 (XP002951542).
Nebergall et al, *College Chemistry with Qualitative Analysis*, 1980, p. 89, pp. 3.

*Primary Examiner* — Taylor Victor Oh
(74) *Attorney, Agent, or Firm* — Mark J. Cohen

(57) ABSTRACT

The present invention is directed to a process, having a reduced environmental impact, for preparing phenylamino substituted quaternary salt compounds that are CCR2 antagonists.

14 Claims, No Drawings

SYNTHESIS OF QUATERNARY SALT COMPOUNDS

CROSS-REFERENCE TO RELATED APPLICATIONS

This Application claims priority to U.S. Provisional Patent Application No. 60/982,802, filed Oct. 26, 2007, which is hereby incorporated by reference in its entirety.

FIELD OF THE INVENTION

The present invention is directed to a process for preparing quaternary chloride salt compounds that are antagonists to the chemoattractant cytokine receptor 2 (CCR2). More particularly, the process is directed to a synthesis of a phenylamino substituted quaternary chloride salt CCR2 antagonist compound wherein said synthesis has a reduced environmental impact.

BACKGROUND OF THE INVENTION

The design of an optimized chemical manufacturing process is very often a process as well, keeping in mind the goals of synthetic efficiency, waste reduction and use of materials having a reduced health risk. A manufacturing synthesis having a reduced environmental impact may employ a safer synthetic design by using minimally hazardous reagents and solvents, thus providing a new, more efficient and cost-effective process with positive environmental and economic impacts. The process of the present invention, while providing a pharmaceutically useful series of compounds, eliminates the use of known mutagenic reagents and chlorinated solvents. Accordingly, the synthesis of the present invention may reduce overall economic and environmental impact by using a reduced amount of reagents and solvents as well as less hazardous reagents and solvents, thereby reducing attendant disposal costs and the total cost of goods.

The synthesis of quaternary ammonium or phosphonium salt forms for a series of 3,4-dihydro-naphthalene, 2H-chromene, 8,9-dihydro-7H-benzocycloheptene and 2,3-dihydro-benzo[b]oxepine carbamoyl compounds as MCP-1 antagonists have been described (see Shiraishi M, Aramaki Y, Seto M, Imoto H, Nishikawa Y, Kanzaki N, Okamoto M, Sawada H, Nishimura O, Baba M and Fujino M, Discovery of Novel, Potent, and Selective Small-Molecule CCR5 Antagonists as Anti-HIV Agents: Synthesis and Biological Evaluation of Anilide Derivatives with a Quaternary Ammonium Moiety, *J. Med. Chem.*, 2000, 43, 2049-2063; see also, U.S. Pat. No. 6,268,354 describing a pharmaceutical composition for antagonizing CCR5 comprising a quaternary ammonium salt form of an anilide derivative).

The synthesis of a salt form for N,N-dimethyl-N-[4-[[[2-(4-methylphenyl)-6,7-dihydro-5H-benzocyclohepten-8-yl]carbonyl]amino]benzyl]tetrahydro-2H-pyran-4-aminium chloride (TAK-779) has been described (see Ikemoto T, Ito T, Hashimoto H, Kawarasaki T, Nishiguchi A, Mitsudera H, Wackimasu M and Tomimatsu K, Development of a New Synthetic Route of a Non-Peptide CCR5 Antagonist, TAK-779, for Large Scale Preparation, *Organic Process Research and Development*, 2000, 4, 520-525; and, Ikemoto T, Nishiguchi A, Mitsudera H, Wakimasu M and Tomimatsu K, Convenient, Efficient Synthesis of TAK-779, a Non-Peptide CCR5 Antagonist: Development of Preparation of Various Ammonium Salts using Trialkylphosphite and N-Halogenosuccinimide, *Tetrahedron*, 2001, 57, 1525-1529)

The synthesis of 7-{4-[2-(butoxy)-ethoxy-phenyl]-N-(4-{methyl-(tetrahydro-2H-pyran-4-yl)amino}methyl]phenyl)-1-propyl-2,3-dihydro-1H-1-benzazepine-4-carboxamide via an acid chloride intermediate has been described (see Ikemoto T, Ito T, Nishiguchi A, Miura S and Tomimatsu K, Practical Synthesis of an Orally Active CCR5 Antagonist, 7-{4-[2-(butoxy)-ethoxy-phenyl]-N-(4-{methyl-(tetrahydro-2H-pyran-4-yl)amino}methyl]phenyl)-1-propyl-2,3-dihydro-1H-1-benzazepine-4-carboxamide, *Organic Process Research and Development*, 2005, 9, 168-173).

United States Patent Publication 2006/0293379, incorporated herein by reference in its entirety and for all purposes, describes substituted quaternary iodide salt compounds of Formula (I) that may be prepared using the process of the present invention. Additionally, all other documents cited herein are incorporated by reference in their entirety and for all purposes.

SUMMARY OF THE INVENTION

The present invention is directed to a process for preparing a quaternary chloride salt compound of Formula (I):

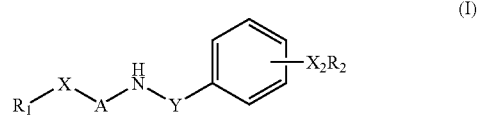

wherein $R_1$, X, A, Y and $X_2R_2$ are as defined herein.

The present invention is also relates to a process for preparing a quaternary chloride salt compound of Formula (Ia):

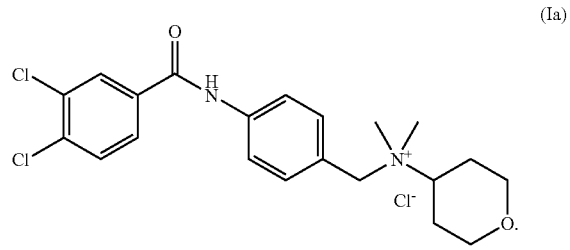

DETAILED DESCRIPTION OF THE INVENTION

The present invention is directed to a process for preparing a quaternary chloride salt compound of Formula (I):

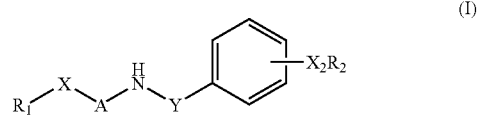

wherein
A is carbonyl;
X is a bond or —CH=CH—;
$R_1$ is selected from aryl, $C_5$-$C_{15}$cycloalkyl or heterocyclyl, wherein said aryl is optionally substituted with one or more lower alkyl, —(CH$_2$)$_n$—CF$_3$, lower alkoxy, alkoxycarbonyl, cyano, halogen or phenyl optionally substituted by lower alkyl, —(CH$_2$)$_n$—CF$_3$, lower alkoxy, alkoxycarbonyl, cyano or halogen, wherein said $C_5$-$C_{15}$cycloalkyl is optionally substituted with one or more lower alkyl, —$(CH_2)_n$—$CF_3$, lower alkoxy, aryl, halogen-substituted aryl, alkoxycarbonyl, cyano or halogen, or wherein said heterocyclyl is optionally substituted with one or more lower alkyl, —$(CH_2)_n$—$CF_3$, lower alkoxy, aryl, aryl-lower alkyl, halogen-substituted aryl, alkoxycarbonyl, cyano or halogen; and wherein n is 0, 1, 2, 3 or 4;

Y is a bond or —$CH_2$—;

$X_2$ is —$(CH_2)_m$—, wherein m is 1 or 2;

$R_2$ is —$N^+(R_4R_5)$—$ZR_3$;

Z is —$(CH_2)_p$— wherein p is 0, 1 or 2;

$R_3$ is selected from aryl, $C_5$-$C_{15}$cycloalkyl or heterocyclyl, wherein said aryl is optionally substituted with one or more lower alkyl, —$(CH_2)_n$—$CF_3$, lower alkoxy, aryl, halogen-substituted aryl, alkoxycarbonyl, cyano or halogen, wherein said $C_5$-$C_{15}$cycloalkyl is optionally substituted with one or more lower alkyl, —$(CH_2)_n$—$CF_3$, lower alkoxy, aryl, halogen-substituted aryl, alkoxycarbonyl, cyano or halogen, or wherein said heterocyclyl is optionally substituted with one or more lower alkyl, —$(CH_2)_n$—$CF_3$, lower alkoxy, aryl, halogen-substituted aryl, alkoxycarbonyl, cyano or halogen; and wherein, when said heterocyclyl is attached via a carbon atom ring member and a heteroatom ring member is adjacent to said carbon atom, then p is 1 or 2; and $R_4$ and $R_5$ are each individually lower alkyl or lower alkenyl; or alternatively, $R_4$ and $R_5$ combine with the nitrogen atom of Formula (I) to form a heterocyclyl ring of 5 to 9 total ring atoms optionally containing an oxygen ring atom, wherein the heterocyclyl ring nitrogen atom is substituted with one of lower alkyl or lower alkenyl to form a quaternary salt, and wherein -$ZR_3$ is absent and the heterocyclyl ring is optionally substituted with aryl optionally substituted with one or more lower alkyl, —$(CH_2)_n$—$CF_3$, lower alkoxy, aryl, halogen-substituted aryl, alkoxycarbonyl, cyano or halogen;

according to Scheme A, comprising the steps of:

Scheme A

Step A. reacting a Compound A1 with a Compound A2, optionally in the presence of an aqueous base, to provide a Compound A3:

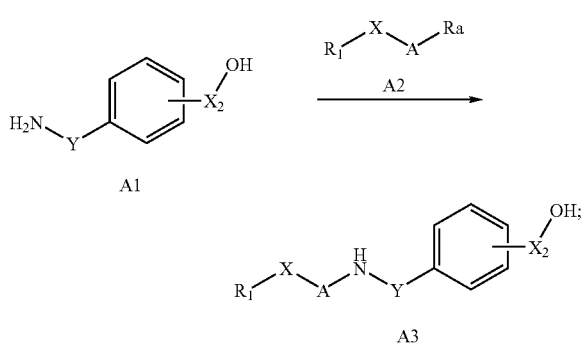

Step B. reacting Compound A3 in the presence of an acid to provide a Compound A4:

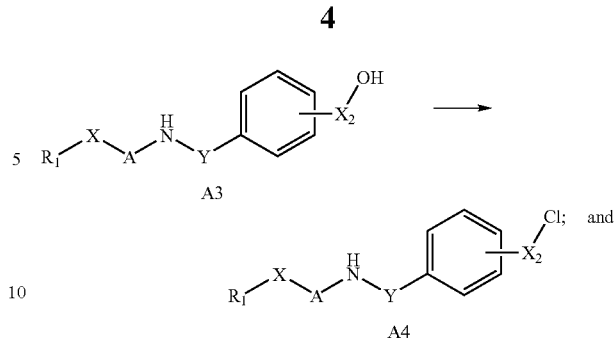

Step C. reacting Compound A4 with a Compound A5 in a solvent to provide Compound A6, representative of the compound of Formula (I):

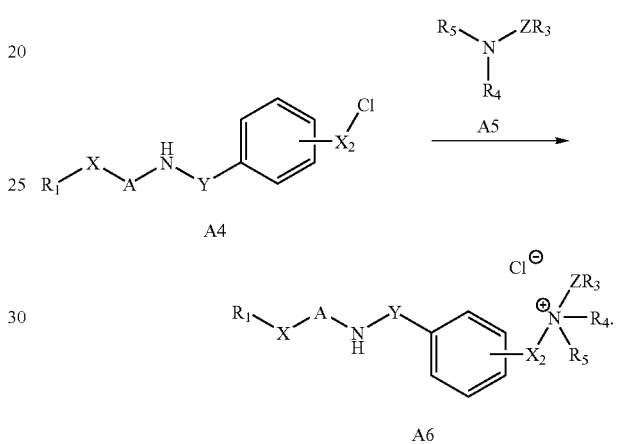

In Step A, the optional aqueous base is $Na_2CO_3$ (at a concentration of about 7.2%) and Compound A1 is reacted with Compound A2 in acetone at a reaction temperature in a range of from about 35° C. to about 42° C.

In Step A, in certain embodiments of the present invention, Compound A1 is reacted with Compound A2 in the presence of $Na_2CO_3$ (at a concentration of about 7.2%) in acetone at a reaction temperature in a range of from about 35° C. to about 42° C.

In Step A the reaction conditions facilitate formation of the amide by directly precipitating the product Compound A3, thus enabling an efficient isolation and work up by cooling the mixture, adding water, and subsequent filtration and drying.

In Step B, Compound A3 is reacted in the presence of an acid such as neat concentrated (conc.) HCl or concentrated HCl in a ratio with a solvent selected from the group consisting of THF, EtOH and acetone at a reaction temperature in a range of from about room temperature (RT) to about 45° C.

In Step B, the ratio of THF: HCl is about 1:1 at a reaction temperature of about RT; wherein the ratio of EtOH: HCl is about 1:1 at a reaction temperature of about RT; and, wherein the ratio of acetone: HCl is about 1:1, or about 3:1, or about 4:1, or about 5.4:1, or about 6:1, or about 7.7:1, or about 12.8:1 at a reaction temperature of about RT, or about 30° C., or about 35° C., or about 40° C., or about 45° C.

In Step B, the acid may also be an inorganic acid chloride such as $SOCl_2$/THF or $SOCl_2$/$CHCl_3$/Pyridine(cat.), as described in the literature (respectively, Ikemoto T, Ito T, Hashimoto H, Kawaraski T, Nishiguchi A, Mitsudera H, Wakimasu M and Tomimatsu K, *Org. Process Res. & Develop.*, 2000, 4, 520; and, Shirashi M, Baba M, Aramaki Y, Hishimura O and Kanzaki N, International Patent Publication WO00/10965) or $PCl_3$, $PCl_5$, $POCl_3$, $SO_2Cl_2$, $Ph_3P$—$CCl_4$ and the like. The acid may further be an organic acid such as oxalyl chloride.

In Step B, the Compound A3 is reacted in the presence of concentrated HCl in a 3:1 ratio with acetone at a reaction temperature in a range of from about 45° C. to about 50° C.

In Step C, Compound A4 is reacted with a Compound A5 in a solvent selected from acetone or EtOH at a reflux temperature that is less than or about the boiling point of the solvent. The reaction conditions facilitate formation of the quaternary chloride salt by directly precipitating the product Compound A6, thus enabling an efficient isolation and work up by cooling the mixture and subsequent filtration and drying.

In Step C, the Compound A4 is reacted with 4-DMATHP Compound B5 in acetone at said reflux temperature.

U.S. Patent Publication 2006/0293379 discloses the following compounds as quaternary iodide salt compounds. The following quaternary chloride salt compounds representative of Formula (I) may be prepared according to the process of the present invention and are selected from the group consisting of:

| Cpd | Name |
|---|---|
| 1 | (E)-(4-{[3-(3-bromo-phenyl)-acryloylamino]-methyl}-benzyl)-cyclohexyl-dimethyl-ammonium chloride, |
| 2 | {4-[(3-bromo-benzoylamino)-methyl]-benzyl}-cyclohexyl-dimethyl-ammonium, chloride |
| 3 | cyclohexyl-dimethyl-{4-[(3-trifluoromethyl-benzoylamino)-methyl]-benzyl}-ammonium chloride, |
| 4 | (E)-(4-{[3-(3,4-dichloro-phenyl)-acryloylamino]-methyl}-benzyl)-dimethyl-(tetrahydro-pyran-4-yl)-ammonium chloride, |
| 5 | (E)-(4-{[3-(3-bromo-phenyl)-acryloylamino]-methyl}-benzyl)-dimethyl-(tetrahydro-pyran-4-yl)-ammonium chloride, |
| 6 | (4-benzoylamino-benzyl)-dimethyl-(tetrahydro-pyran-4-yl)-ammonium chloride, |
| 7 | [3-(3,4-dichloro-benzoylamino)-benzyl]-dimethyl-(tetrahydro-pyran-4-yl)-ammonium chloride, |
| 8 | [3-(3-bromo-benzoylamino)-benzyl]-dimethyl-(tetrahydro-pyran-4-yl)-ammonium chloride, |
| 9 | [4-(2,3-dichloro-benzoylamino)-benzyl]-dimethyl-(tetrahydro-pyran-4-yl)-ammonium chloride, |
| 10 | [4-(2,4-dichloro-benzoylamino)-benzyl]-dimethyl-(tetrahydro-pyran-4-yl)-ammonium chloride, |
| 11 | [4-(2,5-dichloro-benzoylamino)-benzyl]-dimethyl-(tetrahydro-pyran-4-yl)-ammonium chloride, |
| 12 | [4-(2,6-dichloro-benzoylamino)-benzyl]-dimethyl-(tetrahydro-pyran-4-yl)-ammonium chloride, |
| 13 | [4-(2-chloro-benzoylamino)-benzyl]-dimethyl-(tetrahydro-pyran-4-yl)-ammonium chloride, |
| 14 | bicyclo[2.2.1]hept-2-yl-[4-(3,4-dichloro-benzoylamino)-benzyl]-dimethyl-ammonium chloride, |
| 15 | (2S)-[4-(3,4-dichloro-benzoylamino)-benzyl]-dimethyl-(tetrahydro-furan-2-ylmethyl)-ammonium chloride, |
| 16 | (2R)-[4-(3,4-dichloro-benzoylamino)-benzyl]-dimethyl-(tetrahydro-furan-2-ylmethyl)-ammonium chloride, |
| 17 | [4-(3,4-dichloro-benzoylamino)-benzyl]-dimethyl-(tetrahydro-pyran-4-ylmethyl)-ammonium chloride, |
| 18 | [4-(3,4-dichloro-benzoylamino)-benzyl]-ethyl-methyl-(tetrahydro-pyran-4-yl)-ammonium chloride, |
| 19 | [4-(3,4-dichloro-benzoylamino)-benzyl]-methyl-propyl-(tetrahydro-pyran-4-yl)-ammonium chloride, |
| 20 | [4-(3,5-dichloro-benzoylamino)-benzyl]-dimethyl-(tetrahydro-pyran-4-yl)-ammonium chloride, |
| 21 | [4-(3-bromo-benzoylamino)-benzyl]-dimethyl-(tetrahydro-pyran-4-yl)-ammonium chloride, |
| 22 | [4-(3-chloro-2-methyl-benzoylamino)-benzyl]-dimethyl-(tetrahydro-pyran-4-yl)-ammonium chloride, |
| 23 | [4-(3-chloro-4-fluoro-benzoylamino)-benzyl]-dimethyl-(tetrahydro-pyran-4-yl)-ammonium chloride, |
| 24 | [4-(3-chloro-4-methoxy-benzoylamino)-benzyl]-dimethyl-(tetrahydro-pyran-4-yl)-ammonium chloride, |
| 25 | [4-(3-chloro-4-methyl-benzoylamino)-benzyl]-dimethyl-(tetrahydro-pyran-4-yl)-ammonium chloride, |
| 26 | [4-(3-chloro-benzoylamino)-benzyl]-dimethyl-(tetrahydro-pyran-4-yl)-ammonium chloride, |
| 27 | [4-(3-cyano-benzoylamino)-benzyl]-dimethyl-(tetrahydro-pyran-4-yl)-ammonium chloride, |
| 28 | [4-(3-methoxy-benzoylamino)-benzyl]-dimethyl-(tetrahydro-pyran-4-yl)-ammonium chloride, |
| 29 | [4-(4-chloro-2-methyl-benzoylamino)-benzyl]-dimethyl-(tetrahydro-pyran-4-yl)-ammonium chloride, |
| 30 | [4-(4-chloro-3-trifluoromethyl-benzoylamino)-benzyl]-dimethyl-(tetrahydro-pyran-4-yl)-ammonium chloride, |
| 31 | [4-(4-chloro-benzoylamino)-benzyl]-dimethyl-(tetrahydro-pyran-4-yl)-ammonium chloride, |

-continued

| Cpd | Name |
|---|---|
| 32 | [4-(5-chloro-2-methyl-benzoylamino)-benzyl]-dimethyl-(tetrahydro-pyran-4-yl)-ammonium chloride, |
| 33 | {2-[4-(3,4-dichloro-benzoylamino)-phenyl]-ethyl}-dimethyl-(tetrahydro-pyran-4-yl)-ammonium chloride, |
| 34 | {2-[4-(3-bromo-benzoylamino)-phenyl]-ethyl}-dimethyl-(tetrahydro-pyran-4-yl)-ammonium chloride, |
| 35 | (E)-{3-[3-(3-bromo-phenyl)-acryloylamino]-benzyl}-dimethyl-(tetrahydro-pyran-4-yl)-ammonium chloride, |
| 36 | {4-[(3,4-dichloro-benzoylamino)-methyl]-benzyl}-dimethyl-(tetrahydro-pyran-4-yl)-ammonium chloride, |
| 37 | (E)-{4-[3-(3,4-dichloro-phenyl)-acryloylamino]-benzyl}-dimethyl-(tetrahydro-pyran-4-yl)-ammonium chloride, |
| 38 | (E)-{4-[3-(3,5-difluoro-phenyl)-acryloylamino]-benzyl}-dimethyl-(tetrahydro-pyran-4-yl)-ammonium chloride, |
| 39 | (E)-{4-[3-(3-bromo-phenyl)-acryloylamino]-benzyl}-dimethyl-(tetrahydro-pyran-4-yl)-ammonium chloride, |
| 40 | (E)-{4-[3-(3-bromo-phenyl)-acryloylamino]-benzyl}-dimethyl-(tetrahydro-thiopyran-4-yl)-ammonium chloride, |
| 41 | (E)-{4-[3-(3-chloro-phenyl)-acryloylamino]-benzyl}-dimethyl-(tetrahydro-pyran-4-yl)-ammonium chloride, |
| 42 | (E)-{4-[3-(3-fluoro-phenyl)-acryloylamino]-benzyl}-dimethyl-(tetrahydro-pyran-4-yl)-ammonium chloride, |
| 43 | (E)-{4-[3-(4-bromo-phenyl)-acryloylamino]-benzyl}-dimethyl-(tetrahydro-pyran-4-yl)-ammonium chloride, |
| 44 | (E)-1-(4-{[3-(3,4-dichloro-phenyl)-acryloylamino]-methyl}-benzyl)-1-methyl-piperidinium chloride, |
| 45 | (E)-1-(4-{[3-(3-bromo-phenyl)-acryloylamino]-methyl}-benzyl)-1-methyl-piperidinium chloride, |
| 46 | 1-[4-(3,4-dichloro-benzoylamino)-benzyl]-1-methyl-piperidinium chloride, |
| 47 | 1-[4-(3,4-dichloro-benzoylamino)-benzyl]-1-methyl-pyrrolidinium chloride, |
| 48 | (E)-1-{3-[3-(3-bromo-phenyl)-acryloylamino]-benzyl}-1-methyl-piperidinium chloride, |
| 49 | (E)-1-{4-[3-(3,4-dichloro-phenyl)-acryloylamino]-benzyl}-1-methyl-piperidinium chloride, |
| 50 | (E)-1-{4-[3-(3,4-dichloro-phenyl)-acryloylamino]-benzyl}-4-(2-methoxy-phenyl)-1-methyl-piperazin-1-ium chloride, |
| 51 | (E)-1-{4-[3-(3-bromo-phenyl)-acryloylamino]-benzyl}-1-methyl-piperidinium chloride, |
| 52 | 1-methyl-1-[3-(3-trifluoromethyl-benzoylamino)-benzyl]-piperidinium chloride, |
| 53 | (E)-1-methyl-1-{4-[3-(3-trifluoromethyl-phenyl)-acryloylamino]-benzyl}-piperidinium chloride, |
| 54 | (E)-4-(4-{[3-(3,4-dichloro-phenyl)-acryloylamino]-methyl}-benzyl)-4-methyl-morpholin-4-ium chloride, |
| 55 | 4-[4-(3,4-dichloro-benzoylamino)-benzyl]-4-methyl-morpholin-4-ium chloride, |
| 56 | (E)-4-{4-[3-(3,4-dichloro-phenyl)-acryloylamino]-benzyl}-4-methyl-morpholin-4-ium chloride, |
| 57 | (E)-4-{4-[3-(3-bromo-phenyl)-acryloylamino]-benzyl}-4-methyl-morpholin-4-ium chloride, |
| 58 | (E)-4-methyl-4-(4-{[3-(3-trifluoromethyl-phenyl)-acryloylamino]-methyl}-benzyl)-morpholin-4-ium chloride, |
| 59 | (E)-dimethyl-(tetrahydro-pyran-4-yl)-(4-{[3-(3-trifluoromethyl-phenyl)-acryloylamino]-methyl}-benzyl)-ammonium chloride, |
| 60 | dimethyl-(tetrahydro-pyran-4-yl)-[3-(3-trifluoromethyl-benzoylamino)-benzyl]-ammonium chloride, |
| 61 | (E)-dimethyl-(tetrahydro-pyran-4-yl)-[4-(3-m-tolyl-acryloylamino)-benzyl]-ammonium chloride, |
| 62 | dimethyl-(tetrahydro-pyran-4-yl)-[4-(3-trifluoromethyl-benzoylamino)-benzyl]-ammonium chloride, |
| 63 | (E)-dimethyl-(tetrahydro-pyran-4-yl)-{4-[3-(3-trifluoromethyl-phenyl)-acryloylamino]-benzyl}-ammonium chloride, |
| 64 | dimethyl-[4-(3-methyl-benzoylamino)-benzyl]-(tetrahydro-pyran-4-yl)-ammonium chloride, |
| 65 | cycloheptyl-[4-(3,4-dichloro-benzoylamino)-benzyl]-dimethyl-ammonium chloride, |
| 66 | (E)-cyclohexyl-{4-[3-(3,4-dichloro-phenyl)-acryloylamino]-benzyl}-dimethyl-ammonium chloride, |
| 67 | (E)-{4-[3-(3-bromo-phenyl)-acryloylamino]-benzyl}-cyclohexyl-dimethyl-ammonium chloride, |
| 68 | [4-(3-bromo-benzoylamino)-benzyl]-cyclohexyl-dimethyl-ammonium chloride, |
| 69 | cyclohexyl-dimethyl-[4-(3-trifluoromethyl-benzoylamino)-benzyl]-ammonium chloride, |
| 70 | cyclohexyl-[4-(3,4-dichloro-benzoylamino)-benzyl]-dimethyl-ammonium chloride, |
| 71 | [4-(3-chloro-4-fluoro-benzoylamino)-benzyl]-cyclohexyl-dimethyl-ammonium chloride, |
| 72 | cyclohexyl-[4-(2,3-dichloro-benzoylamino)-benzyl]-dimethyl-ammonium chloride, |

| Cpd | Name |
|---|---|
| 73 | cyclohexyl-[4-(2,6-dichloro-benzoylamino)-benzyl]-dimethyl-ammonium chloride, |
| 74 | [4-(3-chloro-4-methoxy-benzoylamino)-benzyl]-cyclohexyl-dimethyl-ammonium chloride, |
| 75 | [4-(3-chloro-4-methyl-benzoylamino)-benzyl]-cyclohexyl-dimethyl-ammonium chloride, |
| 76 | cyclohexyl-[4-(2,5-dichloro-benzoylamino)-benzyl]-dimethyl-ammonium chloride, |
| 77 | cyclopentyl-[4-(3,4-dichloro-benzoylamino)-benzyl]-dimethyl-ammonium chloride, |
| 78 | (E)-cyclohexyl-{3-[3-(3,4-dichloro-phenyl)-acryloylamino]-benzyl}-dimethyl-ammonium chloride, |
| 79 | (E)-cyclohexyl-{3-[3-(4-fluoro-phenyl)-acryloylamino]-benzyl}-dimethyl-ammonium chloride, |
| 80 | dimethyl-(tetrahydro-pyran-4-yl)-{4-[(4'-trifluoromethyl-biphenyl-3-carbonyl)-amino]-benzyl}-ammonium chloride, |
| 81 | cyclohexyl-dimethyl-{4-[(4'-methyl-biphenyl-3-carbonyl)-amino]-benzyl}-ammonium chloride, |
| 82 | dimethyl-{4-[(4'-methyl-biphenyl-3-carbonyl)-amino]-benzyl}-(tetrahydro-pyran-4-yl)-ammonium chloride, |
| 83 | {4-[(biphenyl-4-carbonyl)-amino]-benzyl}-dimethyl-(tetrahydro-pyran-4-yl)-ammonium chloride, |
| 84 | dimethyl-{4-[(naphthalene-1-carbonyl)-amino]-benzyl}-(tetrahydro-pyran-4-yl)-ammonium chloride, |
| 85 | dimethyl-{4-[(naphthalene-2-carbonyl)-amino]-benzyl}-(tetrahydro-pyran-4-yl)-ammonium chloride, |
| 86 | ethyl-methyl-{4-[(naphthalene-2-carbonyl)-amino]-benzyl}-(tetrahydro-pyran-4-yl)-ammonium chloride, |
| 87 | methyl-{4-[(naphthalene-2-carbonyl)-amino]-benzyl}-propyl-(tetrahydro-pyran-4-yl)-ammonium chloride, |
| 88 | {4-[(7-bromo-naphthalene-2-carbonyl)-amino]-benzyl}-dimethyl-(tetrahydro-pyran-4-yl)-ammonium chloride, |
| 89 | {4-[(7-bromo-naphthalene-2-carbonyl)-amino]-benzyl}-cyclohexyl-dimethyl-ammonium chloride, |
| 90 | {4-[(6-bromo-2H-chromene-3-carbonyl)-amino]-benzyl}-dimethyl-(tetrahydro-pyran-4-yl)-ammonium chloride, |
| 91 | {4-[(6-chloro-2H-chromene-3-carbonyl)-amino]-benzyl}-dimethyl-(tetrahydro-pyran-4-yl)-ammonium chloride, |
| 92 | {4-[(6-bromo-2H-chromene-3-carbonyl)-amino]-benzyl}-cyclohexyl-dimethyl-ammonium chloride, |
| 93 | {4-[(6-chloro-2H-chromene-3-carbonyl)-amino]-benzyl}-cyclohexyl-dimethyl-ammonium chloride, |
| 94 | (4-{[(6-bromo-2H-chromene-3-carbonyl)-amino]-methyl}-benzyl)-dimethyl-(tetrahydro-pyran-4-yl)-ammonium chloride, |
| 95 | {4-[(5,7-dichloro-2H-chromene-3-carbonyl)-amino]-benzyl}-dimethyl-(tetrahydro-pyran-4-yl)-ammonium chloride, |
| 96 | cyclohexyl-{4-[(5,7-dichloro-2H-chromene-3-carbonyl)-amino]-benzyl}-dimethyl-ammonium chloride, |
| 97 | {4-[(6,8-dichloro-2H-chromene-3-carbonyl)-amino]-benzyl}-dimethyl-(tetrahydro-pyran-4-yl)-ammonium chloride, |
| 98 | dimethyl-{4-[(6-methyl-2H-chromene-3-carbonyl)-amino]-benzyl}-(tetrahydro-pyran-4-yl)-ammonium chloride, |
| 99 | {4-[(6-methoxy-2H-chromene-3-carbonyl)-amino]-benzyl}-dimethyl-(tetrahydro-pyran-4-yl)-ammonium chloride, |
| 100 | cyclohexyl-dimethyl-{4-[(6-methyl-2H-chromene-3-carbonyl)-amino]-benzyl}-ammonium chloride, |
| 101 | cyclohexyl-{4-[(6-methoxy-2H-chromene-3-carbonyl)-amino]-benzyl}-dimethyl-ammonium chloride, |
| 102 | cyclohexyl-{4-[(6,8-dichloro-2H-chromene-3-carbonyl)-amino]-benzyl}-dimethyl-ammonium chloride, |
| 103 | (2R)-{4-[(6-chloro-2H-chromene-3-carbonyl)-amino]-benzyl}-dimethyl-(tetrahydro-furan-2-ylmethyl)-ammonium chloride, |
| 104 | (2S)-{4-[(6-chloro-2H-chromene-3-carbonyl)-amino]-benzyl}-dimethyl-(tetrahydro-furan-2-ylmethyl)-ammonium chloride, |
| 105 | (2S)-bicyclo[2.2.1]hept-2-yl-{4-[(6-chloro-2H-chromene-3-carbonyl)-amino]-benzyl}-dimethyl-ammonium chloride, |
| 106 | bicyclo[2.2.1]hept-2-yl-{4-[(6,8-dichloro-2H-chromene-3-carbonyl)-amino]-benzyl}-dimethyl-ammonium chloride, |
| 107 | dimethyl-{4-[(8-methyl-2H-chromene-3-carbonyl)-amino]-benzyl}-(tetrahydro-pyran-4-yl)-ammonium chloride, |
| 108 | cyclohexyl-dimethyl-{4-[(8-methyl-2H-chromene-3-carbonyl)-amino]-benzyl}-ammonium chloride, |
| 109 | {4-[(6-chloro-8-methyl-2H-chromene-3-carbonyl)-amino]-benzyl}-cyclohexyl-dimethyl-ammonium chloride, |
| 110 | {4-[(6-chloro-8-methyl-2H-chromene-3-carbonyl)-amino]-benzyl}-dimethyl-(tetrahydro-pyran-4-yl)-ammonium chloride, |
| 111 | cyclohexyl-{4-[(7,8-dichloro-2H-chromene-3-carbonyl)-amino]-benzyl}-dimethyl-ammonium chloride, |

-continued

| Cpd | Name |
|---|---|
| 112 | bicyclo[2.2.1]hept-2-yl-{4-[(6-chloro-8-methyl-2H-chromene-3-carbonyl)-amino]-benzyl}-dimethyl-ammonium chloride, |
| 113 | {4-[(6-chloro-8-methyl-2H-chromene-3-carbonyl)-amino]-benzyl}-cycloheptyl-dimethyl-ammonium chloride, |
| 114 | {4-[(6-chloro-8-methyl-2H-chromene-3-carbonyl)-amino]-benzyl}-cyclopentyl-dimethyl-ammonium chloride, |
| 115 | (4-{[(6-chloro-8-methyl-2H-chromene-3-carbonyl)-amino]-methyl}-benzyl)-dimethyl-(tetrahydro-pyran-4-yl)-ammonium chloride, |
| 116 | cyclohexyl-{4-[(6-fluoro-2H-chromene-3-carbonyl)-amino]-benzyl}-dimethyl-ammonium chloride, |
| 117 | cyclohexyl-{4-[(5-fluoro-2H-chromene-3-carbonyl)-amino]-benzyl}-dimethyl-ammonium chloride, |
| 118 | cyclohexyl-dimethyl-{4-[(6-trifluoromethyl-2H-chromene-3-carbonyl)-amino]-benzyl}-ammonium chloride, |
| 119 | cyclohexyl-{4-[(8-fluoro-2H-chromene-3-carbonyl)-amino]-benzyl}-dimethyl-ammonium chloride, |
| 120 | cyclohexyl-dimethyl-{4-[(7-methyl-2H-chromene-3-carbonyl)-amino]-benzyl}-ammonium chloride, |
| 121 | cyclohexyl-{4-[(7-methoxy-2H-chromene-3-carbonyl)-amino]-benzyl}-dimethyl-ammonium chloride, |
| 122 | {4-[(6-tert-butyl-2H-chromene-3-carbonyl)-amino]-benzyl}-cyclohexyl-dimethyl-ammonium chloride, |
| 123 | cyclohexyl-dimethyl-{4-[(5-trifluoromethyl-2H-chromene-3-carbonyl)-amino]-benzyl}-ammonium chloride, |
| 124 | cyclohexyl-dimethyl-{4-[(8-trifluoromethyl-2H-chromene-3-carbonyl)-amino]-benzyl}-ammonium chloride, |
| 125 | {4-[(3H-benzo[f]chromene-2-carbonyl)-amino]-benzyl}-dimethyl-(tetrahydro-pyran-4-yl)-ammonium chloride, |
| 126 | 1-{4-[(3H-benzo[f]chromene-2-carbonyl)-amino]-benzyl}-1-methyl-pyrrolidinium chloride, |
| 127 | {4-[(3H-benzo[f]chromene-2-carbonyl)-amino]-benzyl}-cyclohexyl-dimethyl-ammonium chloride, |
| 128 | 4-{4-[(3H-benzo[f]chromene-2-carbonyl)-amino]-benzyl}-4-methyl-morpholin-4-ium chloride, |
| 129 | {4-[(3H-benzo[f]chromene-2-carbonyl)-amino]-benzyl}-dimethyl-(tetrahydro-pyran-4-ylmethyl)-ammonium chloride, |
| 130 | (4-{[(3H-benzo[f]chromene-2-carbonyl)-amino]-methyl}-benzyl)-dimethyl-(tetrahydro-pyran-4-yl)-ammonium chloride, |
| 131 | (4-{[(3-bromo-8,9-dihydro-7H-benzocycloheptene-6-carbonyl)-amino]-methyl}-benzyl)-dimethyl-(tetrahydro-pyran-4-yl)-ammonium chloride, |
| 132 | {4-[(3-bromo-8,9-dihydro-7H-benzocycloheptene-6-carbonyl)-amino]-benzyl}-dimethyl-(tetrahydro-pyran-4-yl)-ammonium chloride, |
| 133 | {4-[(3-bromo-8,9-dihydro-7H-benzocycloheptene-6-carbonyl)-amino]-benzyl}-cyclohexyl-dimethyl-ammonium chloride, |
| 134 | 1-{4-[(8,9-dihydro-7H-benzocycloheptene-6-carbonyl)-amino]-benzyl}-1-methyl-pyrrolidinium chloride, |
| 135 | cyclohexyl-{4-[(8,9-dihydro-7H-benzocycloheptene-6-carbonyl)-amino]-benzyl}-dimethyl-ammonium chloride, |
| 136 | {4-[(8,9-dihydro-7H-benzocycloheptene-6-carbonyl)-amino]-benzyl}-dimethyl-(tetrahydro-pyran-4-yl)-ammonium chloride, |
| 137 | (4-{[(8,9-dihydro-7H-benzocycloheptene-6-carbonyl)-amino]-methyl}-benzyl)-dimethyl-(tetrahydro-pyran-4-yl)-ammonium chloride, |
| 138 | dimethyl-(4-{[(2-methyl-5-phenyl-furan-3-carbonyl)-amino]-methyl}-benzyl)-(tetrahydro-pyran-4-yl)-ammonium chloride, |
| 139 | [4-({[5-(4-chloro-phenyl)-2-methyl-furan-3-carbonyl]-amino}-methyl)-benzyl]-dimethyl-(tetrahydro-pyran-4-yl)-ammonium chloride, |
| 140 | dimethyl-{4-[(2-methyl-5-phenyl-furan-3-carbonyl)-amino]-benzyl}-(tetrahydro-pyran-4-yl)-ammonium chloride, |
| 141 | {4-[(benzofuran-2-carbonyl)-amino]-benzyl}-dimethyl-(tetrahydro-pyran-4-yl)-ammonium chloride, |
| 142 | (4-{[5-(4-chloro-phenyl)-2-trifluoromethyl-furan-3-carbonyl]-amino}-benzyl)-dimethyl-(tetrahydro-pyran-4-yl)-ammonium chloride, |
| 143 | (4-{[5-(4-chloro-phenyl)-2-trifluoromethyl-furan-3-carbonyl]-amino}-benzyl)-cyclohexyl-dimethyl-ammonium chloride, |
| 144 | {4-[(5-chloro-benzofuran-2-carbonyl)-amino]-benzyl}-dimethyl-(tetrahydro-pyran-4-yl)-ammonium chloride, |
| 145 | {4-[(5-chloro-benzofuran-2-carbonyl)-amino]-benzyl}-cyclohexyl-dimethyl-ammonium chloride, |
| 146 | {4-[(benzofuran-2-carbonyl)-amino]-benzyl}-cyclohexyl-dimethyl-ammonium chloride, |
| 147 | dimethyl-{4-[(1-methyl-1H-indole-2-carbonyl)-amino]-benzyl}-(tetrahydro-pyran-4-yl)-ammonium chloride, |
| 148 | {4-[(5-chloro-1H-indole-2-carbonyl)-amino]-benzyl}-dimethyl-(tetrahydro-pyran-4-yl)-ammonium chloride, |
| 149 | {4-[(5-bromo-1H-indole-2-carbonyl)-amino]-benzyl}-dimethyl-(tetrahydro-pyran-4-yl)-ammonium chloride, |
| 150 | dimethyl-{4-[(1-methyl-1H-indole-3-carbonyl)-amino]-benzyl}-(tetrahydro-pyran-4-yl)-ammonium chloride, |

| Cpd | Name |
|---|---|
| 151 | {4-[(1-benzyl-1H-indole-3-carbonyl)-amino]-benzyl}-dimethyl-(tetrahydro-pyran-4-yl)-ammonium chloride, |
| 152 | cyclohexyl-dimethyl-{4-[(1-methyl-1H-indole-2-carbonyl)-amino]-benzyl}-ammonium chloride, |
| 153 | {4-[(5-chloro-1H-indole-2-carbonyl)-amino]-benzyl}-cyclohexyl-dimethyl-ammonium chloride, |
| 154 | (2S)-{4-[(5-chloro-1H-indole-2-carbonyl)-amino]-benzyl}-dimethyl-(tetrahydro-furan-2-ylmethyl)-ammonium chloride, |
| 155 | bicyclo[2.2.1]hept-2-ylmethyl-{4-[(5-chloro-1H-indole-2-carbonyl)-amino]-benzyl}-dimethyl-ammonium chloride, |
| 156 | {4-[(7,8-dichloro-2,3-dihydro-benzo[b]oxepine-4-carbonyl)-amino]-benzyl}-dimethyl-(tetrahydro-pyran-4-yl)-ammonium chloride, |
| 157 | cyclohexyl-{4-[(7,8-dichloro-2,3-dihydro-benzo[b]oxepine-4-carbonyl)-amino]-benzyl}-dimethyl-ammonium chloride, |
| 158 | bicyclo[2.2.1]hept-2-yl-{4-[(7,8-dichloro-2,3-dihydro-benzo[b]oxepine-4-carbonyl)-amino]-benzyl}-dimethyl-ammonium chloride, |
| 159 | (4-{[(7,8-dichloro-2,3-dihydro-benzo[b]oxepine-4-carbonyl)-amino]-methyl}-benzyl)-dimethyl-(tetrahydro-pyran-4-yl)-ammonium chloride, |
| 160 | {4-[(3-chloro-benzo[b]thiophene-2-carbonyl)-amino]-benzyl}-dimethyl-(tetrahydro-pyran-4-yl)-ammonium chloride, |
| 161 | {4-[(2,5-dichloro-thiophene-3-carbonyl)-amino]-benzyl}-dimethyl-(tetrahydro-pyran-4-yl)-ammonium chloride, |
| 162 | {4-[(benzo[b]thiophene-2-carbonyl)-amino]-benzyl}-dimethyl-(tetrahydro-pyran-4-yl)-ammonium chloride, |
| 163 | {4-[(benzo[b]thiophene-2-carbonyl)-amino]-benzyl}-cyclohexyl-dimethyl-ammonium chloride, and |
| 164 | {4-[(3-chloro-benzo[b]thiophene-2-carbonyl)-amino]-benzyl}-cyclohexyl-dimethyl-ammonium chloride. |

Discussion of the Invention

As shown in the foregoing Scheme A, the scaled-up process of the present invention differs from the bench-scale process for preparing quaternary iodide salt compounds of Formula (I) disclosed in US Patent Publication 2006/0293379 by enabling the preparation of pharmaceutically useful quaternary chloride salt compounds of Formula (I). The bench-scale process required the use of methyl iodide and an ion-exchange step. As a result, the process disclosed in Publication 2006/029337 was not amenable to scale-up. The instant process described herein is more efficient because the ion-exchange step has been eliminated and less-hazardous because the use of methyl iodide and methylene dichloride has been avoided and the amount of solvents used has been reduced.

Additionally, the process of the present invention differs from the methods of preparation disclosed in the specification and examples in US Patent Publication 2006/029337. Therein, Example 1 described the preparation of a quaternary iodide salt precursor and subsequent conversion to the quaternary chloride salt [4-(3,4-dichloro-benzoylamino)-benzyl]-dimethyl-(tetrahydro-pyran-4-yl)-ammonium chloride Compound 17. The instant process described herein describes the direct preparation of the quaternary ammonium chloride salt of Compound 17, herein referred to as the compound of Formula (Ia).

Moreover, the process of the present invention differs from the Publication 2006/029337, which generally describes the preparation of quaternary iodide salt compounds of Formula (I), by enabling the direct preparation of previously undisclosed quaternary chloride salt compounds of Formula (I).

Accordingly, the instant process enables the direct preparation of quaternary chloride salt compounds of Formula (I).

The present invention also relates to a process for preparing a quaternary chloride salt compound of Formula (Ia):

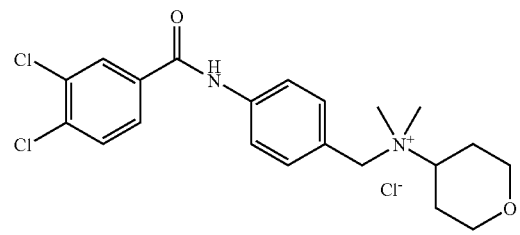

wherein the compound of Formula (Ia) is described in U.S. Patent Publication 2006/0293379 and referred to as [4-(3,4-dichloro-benzoylamino)-benzyl]-dimethyl-(tetrahydro-pyran-4-yl)-ammonium chloride Compound 17.

The present invention is further directed to a process for providing the compound of Formula (Ia) as represented by Scheme B.

Scheme B

A process for preparing a quaternary chloride salt compound of Formula (Ia):

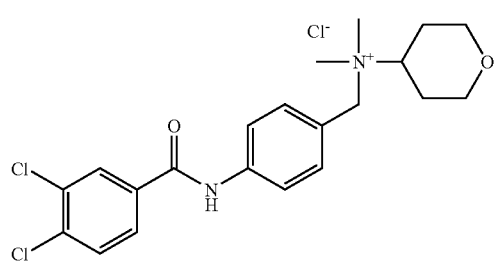

comprising the steps of:

Step A. reacting a Compound B1 with a Compound B2, optionally in the presence of an aqueous base, to provide a Compound B3:

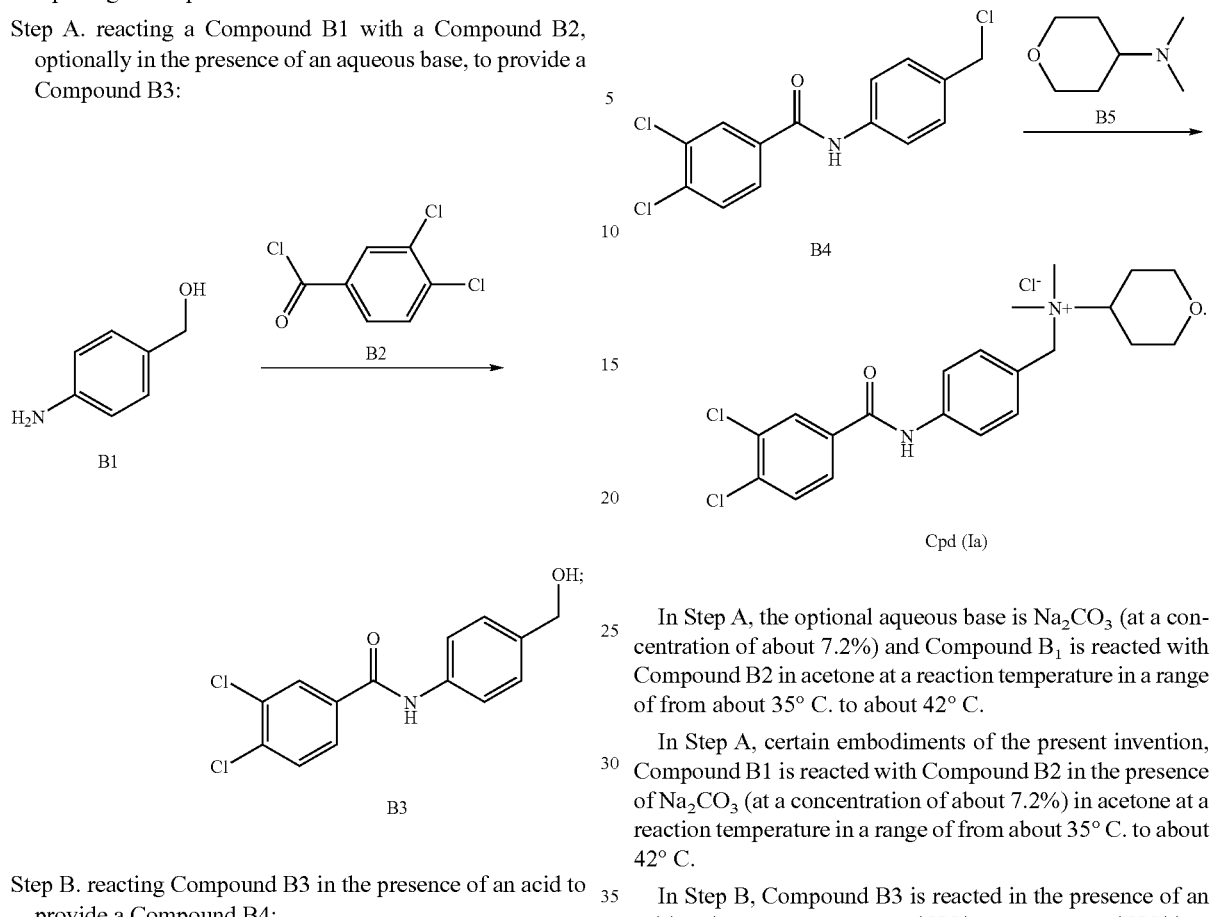

Step B. reacting Compound B3 in the presence of an acid to provide a Compound B4:

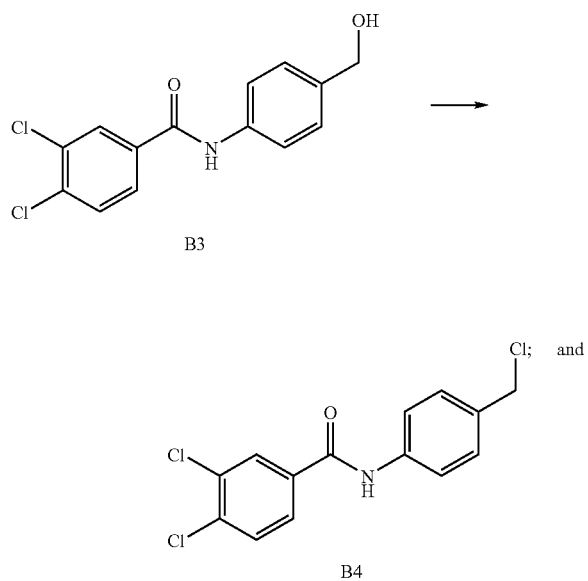

Step C. reacting Compound B4 with 4-(dimethylamino)tetrahydropyran (4-DMATHP) Compound B5 in a solvent to provide the compound of Formula (Ia), representative of the compound of Formula (I):

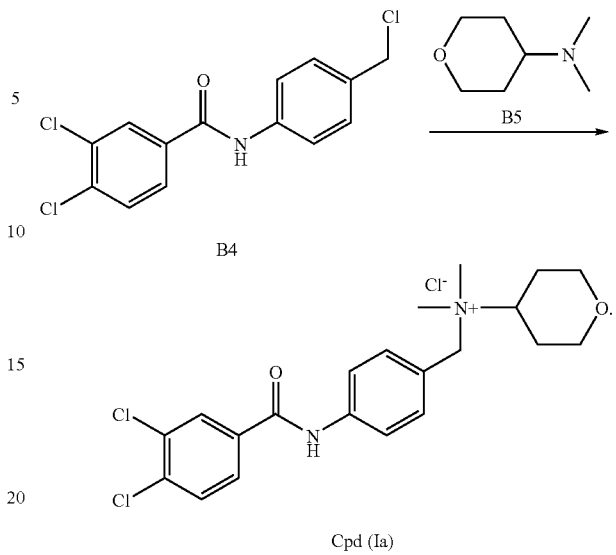

In Step A, the optional aqueous base is $Na_2CO_3$ (at a concentration of about 7.2%) and Compound $B_1$ is reacted with Compound B2 in acetone at a reaction temperature in a range of from about 35° C. to about 42° C.

In Step A, certain embodiments of the present invention, Compound B1 is reacted with Compound B2 in the presence of $Na_2CO_3$ (at a concentration of about 7.2%) in acetone at a reaction temperature in a range of from about 35° C. to about 42° C.

In Step B, Compound B3 is reacted in the presence of an acid such as neat concentrated HCl or concentrated HCl in a ratio with a solvent selected from the group consisting of THF, EtOH and acetone at a reaction temperature in a range of from about room temperature (RT) to about 45° C.

In Step B, the ratio of THF: HCl is about 1:1 at a reaction temperature of about RT; wherein the ratio of EtOH: HCl is about 1:1 at a reaction temperature of about RT; and, wherein the ratio of acetone: HCl is about 1:1, or about 3:1, or about 4:1, or about 5.4:1, or about 6:1, or about 7.7:1, or about 12.8:1 at a reaction temperature of about RT, or about 30° C., or about 35° C., or about 40° C., or about 45° C.

In Step B, the acid may also be an inorganic acid chloride such as $SOCl_2$/THF or $SOCl_2$/$CHCl_3$/Pyridine(cat.), (see above, Ikemoto T et al, and Shirashi M et al) or $PCl_3$, $PCl_5$, $POCl_3$, $SO_2Cl_2$, $Ph_3P$-$CCl_4$ and the like. The acid may further be an organic acid such as oxalyl chloride.

In Step B, the Compound B3 is reacted in the presence of concentrated HCl in a 3:1 ratio with acetone at a reaction temperature in a range of from about 45° C. to about 50° C.

In Step C, Compound B4 is reacted with 4-DMATHP Compound B5 in a solvent selected from acetone or EtOH at a reflux temperature that is less than or about the boiling point of the solvent.

In Step C, the Compound B4 is reacted with Compound B5 in acetone at said reflux temperature.

The present invention is also directed to intermediate compounds useful in the instant process selected from the group consisting of:

| Cpd | Name |
|---|---|
| B3 | 3,4-dichloro-N-(4-hydroxymethyl-phenyl)-benzamide, and |
| B4 | 3,4-dichloro-N-(4-chloromethyl-phenyl)-benzamide. |

The foregoing schemes are offered by way of illustration; the invention should not be construed as being limited by the chemical reactions and conditions expressed. The methods for preparing the various starting materials used in the schemes are within the skill of persons versed in the art.

Chemical Definitions

Bond lines drawn into a ring system from a substituent variable indicate that the substituent may be attached to any of the substitutable ring atoms.

As used herein, the following terms are intended to have the following definitions:

The term "alkyl" means a saturated aliphatic branched or straight-chain monovalent hydrocarbon radical or linking group substituent having 1-8 carbon atoms. The term includes an alkyl substituent having 1-4 carbon atoms (i.e. lower alkyl). An alkyl radical is derived by the removal of one hydrogen atom from a carbon atom and the linking group is derived by the removal of one hydrogen atom from each of two carbon atoms in the chain. The term includes, without limitation, methyl, methylene, ethyl, ethylene, propyl, propylene, isopropyl, isopropylene, n-butyl, n-butylene, t-butyl, t-butylene, pentyl, pentylene, hexyl, hexylene and the like. An alkyl substituent may be attached to a core molecule via a terminal carbon atom or via a carbon atom within the chain. Similarly, any number of substituent variables may be attached to an alkyl substituent when allowed by available valences.

The term "alkenyl" means an alkyl radical or linking group substituent having 2-8 carbon atoms and at least one double bond derived by the removal of one hydrogen atom from each of two adjacent carbon atoms in the chain. The term includes an alkenyl substituent having 2-4 carbon atoms. The term includes, without limitation, methylidene, vinyl, vinylidene, allyl, allylidene, propylidene, isopropenyl, iso-propylidene, prenyl, prenylene (3-methyl-2-butenylene), methallyl, methallylene, allylidene (2-propenylidene), crotylene (2-butenylene), and the like. An alkenyl substituent may be attached to a core molecule via a terminal carbon atom or via a carbon atom within the chain. Similarly, any number of substituent variables may be attached to an alkenyl substituent when allowed by available valences.

The term "alkoxy" means an alkyl radical or linking group substituent attached through an oxygen-linking atom, wherein the radical is of the formula —O-alkyl and a linking group is of the formula —O-alkyl-. The term includes, without limitation, methoxy, ethoxy, propoxy, butoxy and the like. An alkoxy substituent may be attached to a core molecule and further substituted where allowed by available valences.

The term "cycloalkyl" means a saturated or partially unsaturated monocyclic, polycyclic or bridged hydrocarbon ring system radical or linking group. A ring of 3 to 20 carbon atoms may be designated by $C_{3-20}$ cycloalkyl; a ring of 3 to 12 carbon atoms may be designated by $C_{3-12}$ cycloalkyl, a ring of 3 to 8 carbon atoms may be designated by $C_{3-8}$ cycloalkyl and the like. A cycloalkyl substituent may be attached to a core molecule and further substituted where allowed by available valences.

The term cycloalkyl includes, without limitation, cyclopropyl, cyclobutyl, cyclopentyl, cyclohexyl, cyclohexenyl, cycloheptyl, cyclooctyl, indanyl, indenyl, 1,2,3,4-tetrahydro-naphthalenyl, 5,6,7,8-tetrahydro-naphthalenyl, 8,9-dihydro-7H-benzocyclohepten-6-yl, 6,7,8,9-tetrahydro-5H-benzocycloheptenyl, 5,6,7,8,9,10-hexahydro-benzocyclooctenyl, fluorenyl, bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantanyl, octahydro-4,7-methano-1H-indenyl, octahydro-2,5-methano-pentalenyl (also referred to as hexahydro-2,5-methano-pentalenyl) and the like.

The term "aryl" means an unsaturated, conjugated π electron monocyclic or polycyclic hydrocarbon ring system radical or linking group substituent of 6, 9, 10 or 14 carbon atoms. The term includes, without limitation, phenyl, naphthalenyl, fluorenyl, azulenyl, anthracenyl and the like. An aryl substituent may be attached to a core molecule and further substituted where allowed by available valences.

The term heterocyclyl includes, without limitation, furanyl, thienyl, 2H-pyrrolyl, 2-pyrrolinyl, 3-pyrrolinyl, pyrrolidinyl, pyrrolyl, 1,3-dioxolanyl, oxazolyl, thiazolyl, imidazolyl, 2-imidazolinyl (also referred to as 4,5-dihydro-1H-imidazolyl), imidazolidinyl, 2-pyrazolinyl, pyrazolidinyl, pyrazolyl, isoxazolyl, isothiazolyl, oxadiazolyl, triazolyl, thiadiazolyl, tetrazolyl, tetrazolinyl, tetrazolidinyl, 2H-pyranyl, 4H-pyranyl, thiopyranyl, pyridinyl, piperidinyl, 1,4-dioxanyl, morpholinyl, 1,4-dithianyl, thiomorpholinyl, pyridazinyl, pyrimidinyl, pyrazinyl, piperazinyl, azetidinyl, azepanyl, indolizinyl, indolyl, isoindolyl, 3H-indolyl, indolinyl, benzofuranyl, benzo[b]thienyl, 1H-indazolyl, benzoimidazolyl, benzothiazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl, quinuclidinyl, 2H-chromenyl, 3H-benzo [f]chromenyl, tetrahydro-furanyl, tetrahydro-thienyl, tetrahydro-pyranyl, tetrahydro-thiopyranyl, tetrahydro-pyridazinyl, hexahydro-1,4-diazepinyl, hexahydro-1,4-oxazepanyl, 2,3-dihydro-benzo[b]oxepinyl, 1,3-benzodioxolyl (also known as 1,3-methylenedioxyphenyl), 2,3-dihydro-1,4-benzodioxinyl (also known as 1,4-ethylenedioxyphenyl), benzo-dihydro-furanyl (also known as 2,3-dihydro-benzofuranyl), benzo-tetrahydro-pyranyl, benzo-dihydro-thienyl, 5,6,7,8-tetrahydro-4H-cyclohepta[b]thienyl, 5,6,7-trihydro-4H-cyclohexa[b]thienyl, 5,6-dihydro-4H-cyclopenta[b]thienyl, 2-aza-bicyclo[2.2.1]heptyl, 1-aza-bicyclo[2.2.2]octyl, 8-aza-bicyclo[3.2.1]octyl, 7-oxa-bicyclo[2.2.1]heptyl, pyrrolidinium, piperidinium, piperazinium, morpholinium and the like.

The term "carbonyl" means a linking group having the formula —C(O)— or —C(=O)—.

The term "thiocarbonyl" means a linking group having the formula —C(S)— or —C(=S)—.

The term "sulfonyl" means a linking group having the formula —$SO_2$—.

The term "alkoxycarbonyl" means a radical having the formula —C(O)O-alkyl.

The term "halo" or "halogen" means one or more fluoro, chloro, bromo or iodo atom radicals.

The term "substituted" means one or more hydrogen atoms on a core molecule have been replaced with one or more radicals or linking groups, wherein the linking group, by definition is also further substituted.

The term "about", either used explicitly or impliedly preceding a quantitative value, means the approximation to said value which one skilled in the art would reasonably infer due to variations in experimental conditions and/or measurements for said value.

The substituent nomenclature used in the disclosure of the present invention was derived using IUPAC rules.

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore, when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative salts include the following: acetate, adipate, benzenesulfonate, benzoate, bicarbonate, bisulfate, bitartrate, borate, bromide, calcium, camsylate (or camphosulphonate), carbonate, chloride, clavulanate, citrate, dihydrochloride, edetate, fumarate, gluconate, glutamate, glyconate, hydrabamine, hydrobromine, hydrochloride, iodide, isothionate, lactate, malate, maleate, malonate, mandelate, mesylate, nitrate, oleate, pamoate, palmitate, phosphate/diphosphate, saccharinate, salicylate, stearate, sulfate, succinate, tartrate, tosylate, trichloroacetate, trifluoroacetate and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and P. G. M. Wuts and T. W. Greene, *Protective Groups in Organic Synthesis*, 4th Edition, John Wiley & Sons, 2007. The protecting groups may be removed at a convenient subsequent stage using methods known in the art. The scope of the present invention encompasses all such protected compound forms and mixtures thereof.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "geometric isomer" means isomers that differ in the orientation of substituent atoms in relationship to a carbon-carbon double bond, to a cycloalkyl ring, or to a bridged bicyclic system.

Substituent atoms (other than hydrogen) on each side of a carbon-carbon double bond may be in an E or Z configuration according to the Cahn-Ingold-Prelog system sequence rules which rank the two substituent groups at each carbon atom. In the "E" configuration, the two higher ranking substituents are on opposite sides in relationship to the carbon-carbon double bond. In the "Z" configuration, the two higher ranking substituents are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

Accordingly, the descriptors ("R," "S," "E," and "Z") indicate isomeric atom configurations and are intended to be used as defined in the literature.

Furthermore, compounds of the present invention may have at least one crystalline, polymorph or amorphous form. The plurality of such forms are included in the scope of the invention. In addition, some of the compounds may form solvates with water (i.e., hydrates) or common organic solvents (e.g., organic esters such as ethanolate and the like). The plurality of such solvates are also intended to be encompassed within the scope of this invention.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Synthetic Methods

Representative compounds of the present invention can be synthesized in accordance with the general synthetic schemes described herein and as illustrated more particularly in the specific examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art.

The following abbreviations and formulas have the indicated meanings:

| Abbreviation | Meaning |
| --- | --- |
| ACN or MeCN | Acetonitrile |
| Cpd | Compound |
| 4-DMATHP | 4-(dimethylamino)tetrahydropyran |
| EtOH | Ethanol |
| HPLC | High Pressure Liquid Chromatography |
| MEK | methyl ethyl ketone |
| min(s)/hr(s)/d(s) | minute(s)/hour(s)/day(s) |
| MS | mass spectrum, refers to data shown as m/z $(M + H)^+$ |
| RBF | round bottom flask |
| RT/rt/r.t./RH | room temperature/relative humidity |
| THF | Tetrahydrofuran |

EXAMPLE 1

[4-(3,4-dichloro-benzoylamino)-benzyl]-dimethyl-(tetrahydro-pyran-4-yl)-ammonium chloride Cpd (Ia)

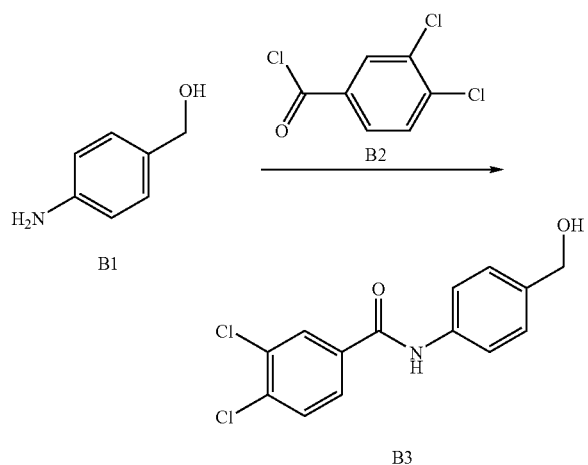

To a 5 L RBF equipped with an overhead stirrer, water (3.586 kg) and sodium carbonate (0.276 kg, 2.61 mol; 7.16% w/total w) were added and stirred. Compound B1 (0.544 kg, 4.33 mol) was added and the mixture was stirred for 30 minutes at RT. The reaction mixture was filtered through a coarse sintered glass filter into a 22 L Morton RBF. The solution was hazy-grey in color with a small amount of insoluble material.

3,4-dichlorobenzoyl chloride Compound B2 (0.900 kg, 4.17 mol) was melted and dissolved in acetone (0.369 kg). The resulting solution was added over a period of 60-90 minutes with stirring. The product immediately precipitated upon addition of the Compound B2 solution. The addition was exothermic and the temperature was allowed to increase to a maximum of 45° C. The reaction was complete when $^1$HNMR showed no absorbance for Compound B2. Water (3.586 kg) was added to the resulting slurry, which was stirred for 30 minutes, then filtered and washed with water (3.586 kg). The filter cake was air dried for about 1 hour, transferred to a vacuum oven and dried at 50-60° C. under full vacuum overnight, with a slight nitrogen bleed. The crude Compound B3 was isolated (1.300 kg, 104% mass yield, 90.6 area.%) as a tan solid.

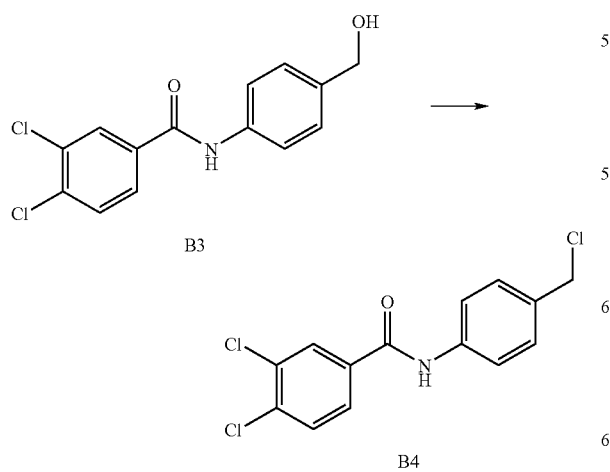

To a 22 L Morton RBF equipped with an overhead stirrer, thermocouple, heating/cooling bath, condenser and an addition vessel was added acetone (4.000 kg) and Compound B3 (1.250 kg, 3.80 mol) using a powder addition funnel. The funnel was rinsed with acetone (0.516 kg). The slurry was stirred and heated to 40-45° C., then 37% HCl (1.123 kg, 11.40 mol) was added over a 5 minute period using the addition vessel. The reaction mixture was a thin slurry after the 37% HCl addition (40-45° C.).

The mixture was stirred at 40-45° C. until the reaction was complete as shown by HPLC. Water (5.710 kg) was added to the slurry, which was cooled to 20-25° C. and stirred for 30 minutes. The solids were filtered and the filter cake was washed with water (5.710 kg) water. The filter cake was air dried for about 1 hour and then transferred to a vacuum oven and dried at 40-50° C. under full vacuum overnight with a slight nitrogen bleed. The crude Compound B4 was isolated (1.251 kg, 104% mass yield, 89.1% area) as a tan solid.

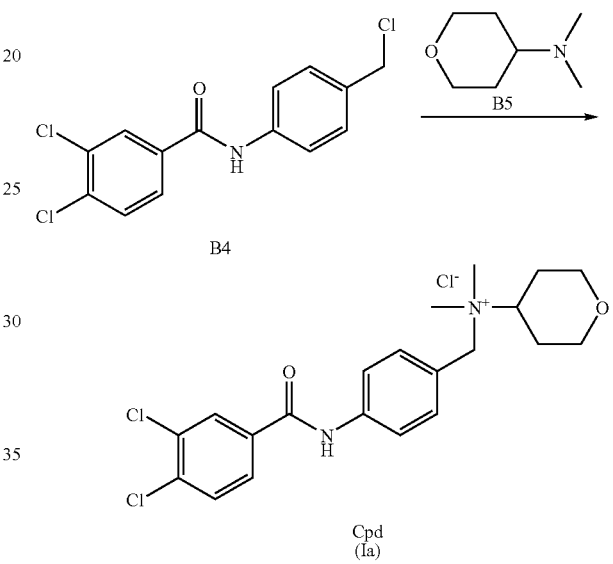

To a 22 L RBF equipped with an overhead stirrer, thermocouple, powder addition funnel, and a heating/cooling bath was added acetone (9.500 kg) and Compound B4 (2.430 kg, 6.95 mol). The slurry was stirred at 40-50° C. for at least 30 minutes. Any insoluble solids were filtered through a coarse glass sintered filter directly into a 50 L Morton RBF equipped with an overhead stirrer, thermocouple, heating/cooling bath, condenser and an addition vessel. 4-DMATHP Compound B5 (1.043 kg, 7.67 mol) was added with continued heating over a period of about 30 minutes to the reaction mixture. The resulting solution/slurry was heated to reflux until reaction completion. When the reaction was complete, as shown by HPLC analysis, the reaction suspension was cooled to RT and the solids were filtered. The filter cake was washed with acetone (12.50 kg), air dried for about 1 hour and then transferred to a vacuum oven and dried at 70-80° C. under full vacuum overnight with a slight nitrogen bleed. The compound of Formula (Ia) was isolated (2.994 kg, 96% mass yield, 99.5% area) as a white solid: m.p. 239.0-241.5° C.

EXAMPLE 2

[4-(3,4-dichloro-benzoylamino)-benzyl]-dimethyl-(tetrahydro-pyran-4-yl)-ammonium chloride Cpd (Ia)

Example 2 represents a scaleable purification process for the compound of Formula (Ia).

The compound of Formula (Ia) in situ with impurity Compound B4 was refluxed in EtOH (5X) with 4-DMATHP Compound B5 (5% by weight) until the level of Compound B4 was less than 5 ppm. The resulting suspension was cooled to room temperature and acetone (5×) was added. The suspension was cooled down to 0-5° C. and stirred for 2 hours. The product was filtered and washed with acetone (2×) under N₂ protection. The wet product was dried at 45° C. under full vacuum overnight.

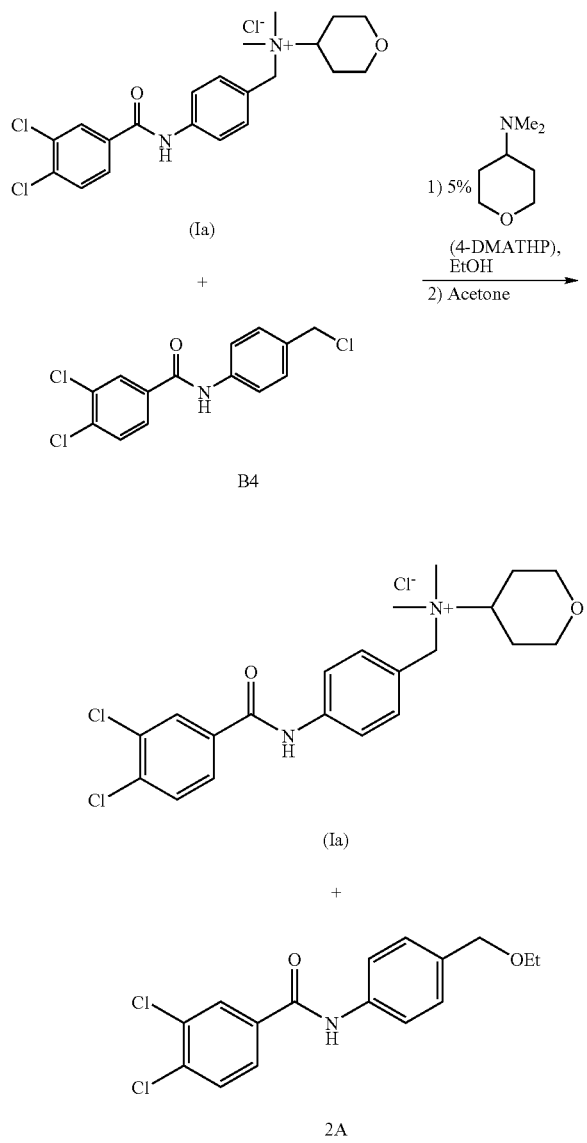

To a 1000 mL three-necked round bottom vessel equipped with a mechanical stirrer, and condenser and thermocouple was added absolute ethanol (197.25 g, 4281.53 mmol). The ethanol was agitated, then a crude mixture of the compound of Formula (Ia) (50.00 g, 112.67 mmol) and 4-DMATHP Compound B5 (2.50 g, 19.35 mmol, 5 wt %) were added to the suspension. The reaction mixture was heated to reflux and agitated until the reaction was complete. A very thin suspension was obtained.

To monitor the reaction, an aliquot (0.5 mL) was removed hourly and diluted with 1 mL ACN to check the amount of impurity Compound B4. The aliquot was cooled to room temperature and an equal volume of acetone was added. The solid was filtered and analyzed for residual impurity Compound B4 in the wet cake to ensure that the amount was less than 5 ppm.

Once the reaction was complete, the reaction mixture was cooled to 20-25° C. The product started to precipitate at 46° C. to afford a thick suspension at room temperature. Acetone (197.75 g, 3404.79 mmol) was added to the suspension, which was cooled to from about 0° C. to about 5° C. and agitated for 2-3 hours. The product was filtered under N₂ protection and washed with acetone (79.10 g, 1361.91 mmol). The damp product was dried in a vacuum oven overnight under full vacuum at 45° C. to afford the purified compound of Formula (Ia) (30.0 g) as a white solid.

EXAMPLE 3

[4-(3,4-dichloro-benzoylamino)-benzyl]-dimethyl-(tetrahydro-pyran-4-yl)-ammonium chloride Cpd (Ia)

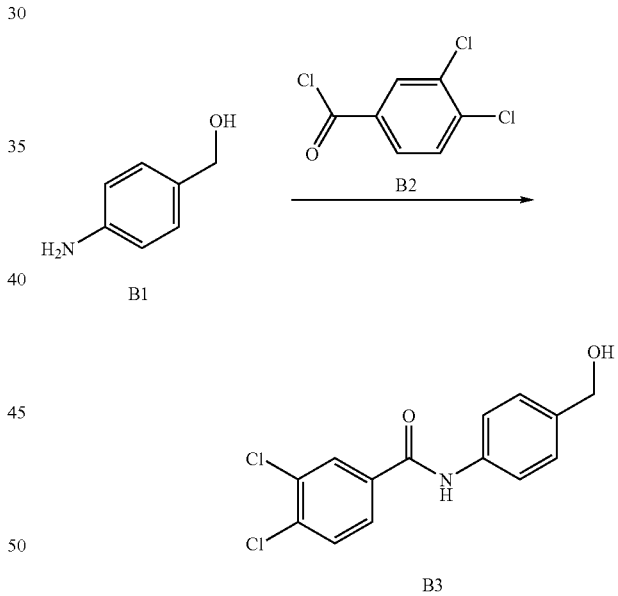

4-aminobenzyl alcohol Compound B1 (20.0 g, 162.4 mmol) and sodium carbonate (15.6 g, 147.2 mmol) were suspended in water (130.0 g) at 20-30° C. A solution of 3,4-dichlorobenzoyl chloride Compound B2 (30.9 g, 147.5 mmol) in acetone (12.5 g) was added over a period of 40-60 min at 25-30° C. (slightly exothermic reaction) with vigorous stirring. The suspension was stirred for another 1-2 hrs at 25-30° C., then 1-2 hrs at 40-50° C. and diluted with water (130.0 g). The mixture was cooled to 20° C. and stirred for another 15-45 min at 18-25° C. The solids were filtered off, washed with water (130.0 g) and dried at 60° C. under vacuum to provide Compound B3 (40.1 g, 92%) as a white powder.

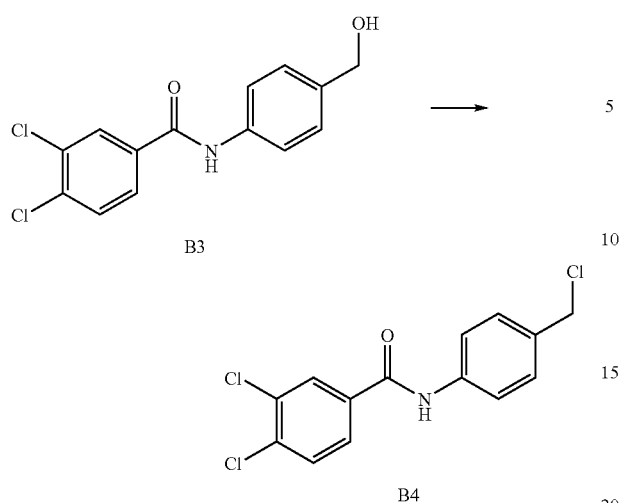

Compound B3 (50.0 g, 168.8 mmol) was suspended in ACN (250.0 g) at 25-30° C. Thionyl chloride (22.1 g, 185.7 mmol) was added over a period of 30-45 min with vigorous stirring at 25-35° C. The resulting thick suspension was stirred for another 2-3 hrs at 30-35° C. until completion. The reaction mixture was cooled to 20-25° C. and water (300.0 g) was added. The mixture was stirred for another 30-60 min, the solids were filtered off and washed with water (300.0 g), then dried at 60° C. under vacuum to provide Compound B4 (48.0 g, 90%) as a yellowish powder.

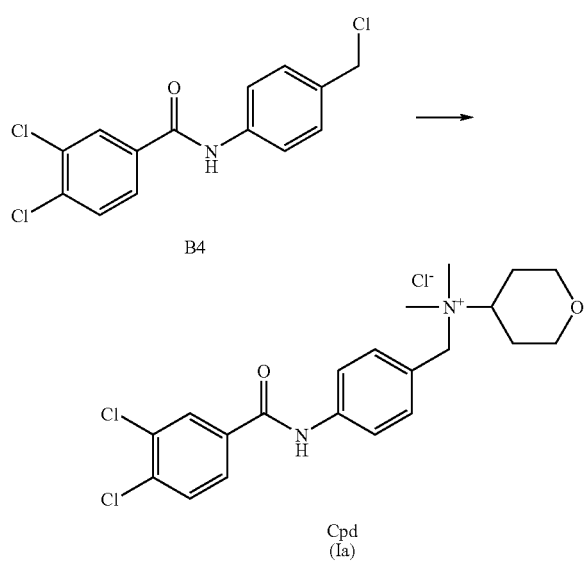

Compound B4 (40.0 g, 127.3 mmol) was suspended in acetone (240.0 g) at a temperature of from about 45° C. to about 55° C. 4-DMATHP Compound B5 (18.0 g, 139.3 mmol) was added over a period of 15-30 min (exothermic reaction). The suspension was stirred for 3-4 h at reflux until the reaction was complete and cooled to 20-25° C. with stirring for another 30-60 min. The solids were filtered off, washed with acetone (240.0 g) and dried at 60° C. under vacuum to provide the compound of Formula (Ia) (51.3 g, 91%) as a white powder.

The compound of Formula (Ia) (40.0 g, 90.1 mmol) was dissolved in (200.0 g) absolute ethanol at 70-78° C., followed by a clear filtration. The solvent (170-180 g) was distilled off and the product crystallized. At 70-78° C., MEK (200.0 g) was added over a period of 15-30 min (exothermic reaction) and a final crystallization started immediately. The suspension was stirred for 3-4 h at reflux until completion. The reaction mixture was cooled to 20-25° C. and stirred for another 30-60 min. The solids were filtered off and washed with MEK (120.0 g), then dried at 60° C. under vacuum to provide the compound of Formula (Ia) (38.4 g, 96%) as a white powder.

EXAMPLE 4

[4-(3,4-dichloro-benzoylamino)-benzyl]-dimethyl-(tetrahydro-pyran-4-yl)-ammonium chloride Cpd (Ia)

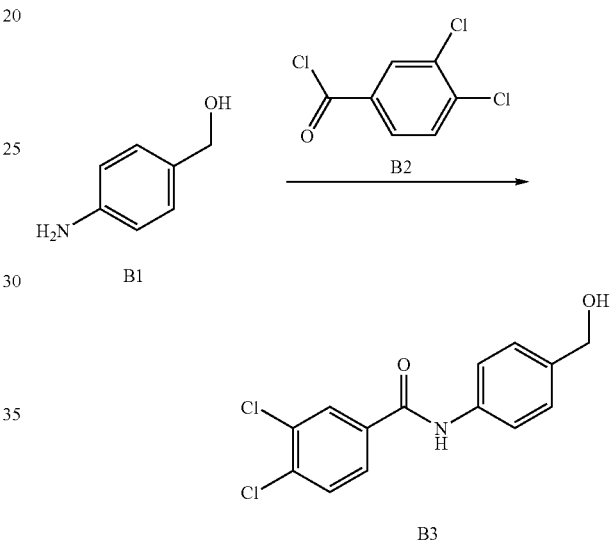

A 5 L 4-neck Morton flask was equipped with an overhead stirrer, thermocouple, heating/cooling bath, and an addition funnel. A mixture of $Na_2CO_3$ (101.15 g, 954.43 mmol) and water (900.00 g) was added to the flask and stirred to effect solution. Compound B1 (150.77 g, 1200.00 mmol) was also added and the mixture was stirred and heated to a temperature of from about 40° C. to about 42° C. to dissolve Compound B1. The resulting dark orange-brown reaction mixture was stirred during the addition of a solution of Compound B2 (249.55 g, 1 155.65 mmol) in acetone (103.00 g). The addition required 50 minutes at ambient temperature (from about 32° C. to about 42° C.) during which time the product Compound B3 continually precipitated as a granular, tan solid. The reaction was monitored by HPLC analysis and was complete after the addition of Compound B2. There was <2% by area of Compound B1 relative to the product, Compound B3.

Water (850.00 g) was added to the reaction suspension to complete the precipitation of Compound B3. The suspension was stirred for about 30 minutes and cooled to a temperature of about 2° C. to about 3° C. in an ice bath. The suspension was filtered and the tan solid was washed twice with water (200.00 g, 225.00 g) and then air dried. HPLC analysis of the damp product showed evidence for a small amount of 3,4-dichlorobenzoic acid (DCBA) as an impurity, which was removed by stirring a slurry of the damp product in a solution of $Na_2CO_3$ (101.20 g, 954.90 mmol) and water (900.00 g) for about 1 hour at ambient temperature. The suspension was filtered and the solid was washed three times with warm water (500.00 g each) (at a temperature of about 45° C. to about 50° C.) and air dried to recover Compound B3 (332.92 g, 1075.00 mmol) as a granular, tan solid. HPLC analysis: 97.6% by area.

The crude product Compound B3 may be further purified if necessary. A suspension of crude Compound B3 (24.60 g, 83.07 mmol) in THF (155.58 g) was stirred at RT for about 20 minutes and then filtered to remove any insoluble material. The filtrate was heated to about 30° C. to redissolve any Compound B3 that precipitated followed by addition of n-heptane (478.80 g). The product precipitated and the suspension was stirred for 20 minutes and then filtered. The solid was washed with n-heptane (34.20 g) and was dried at about 60° C. at full vacuum overnight to recover purified Compound B3 (20.50 g, 69.22 mmol). $^1$H NMR (300 MHz, DMSO-$d_6$): δ 10.37 (s, 1H), 8.22 (d, J=2.0 Hz, 1H), 7.94 (dd, J=8.4, 2.1 Hz, 1H), 7.82 (d, J=8.4 Hz, 1H), 7.70, (d, J=8.5 Hz, 2H), 7.30 (d, J=8.5 Hz, 2H), 5.16 (t, J=5.7 Hz, 1H), 4.47 (d, J=5.6 Hz, 2H); MS: (CI): m/z 296 (M$^+$+1); Anal. Calcd for $C_{14}H_{11}Cl_2NO_2$: C, 56.78; H, 3.74; N, 4.73; Cl, 23.94. Found: C, 56.70; H, 3.53; N, 4.65; Cl, 23.60.

A 3 L 4-neck Morton flask was equipped with an overhead stirrer, thermocouple, heating mantle and an addition funnel. The flask was charged with Compound B3 (109.45 g, 304.16 mmol) followed by acetone (356.40 g). The resultant amber-yellow suspension was stirred and heated to a temperature of about 47° C. to about 48° C. whereupon much of the starting Compound B3 dissolved to afford a thin slurry. 37% HCl (90.00 g, 913.33 mmol) was added to the slurry over a period of about 5 minutes while maintaining the temperature at about 46° C. to about 48° C. After the addition was complete a slightly turbid, dark amber solution resulted from which the product Compound B4 began to precipitate within about 30 to about 40 minutes. After about 1 hour, acetone (39.60 g) was added to facilitate stirring and the resulting thick, cream suspension was stirred at a temperature of from about 45° C. to about 49° C. The reaction was monitored by HPLC and was judged to be complete after about 7 hours when the amount of Compound B3 relative to Compound B4 was <5% by area.

The suspension was cooled to RT and diluted slowly by addition of water (450.00 g). The resultant light tan suspension was stirred at ambient temperature for about 30 minutes. The suspension was settled for a few minutes and then filtered. The solid was washed twice with water (225.00 g each) and then air dried overnight to afford Compound B4 (107.84 g, 342.78 mmol) as a light tan powder. HPLC analysis: 98.0% by area with 2% by area residual B3. $^1$H NMR (300 MHz, DMSO-$d_6$): δ 10.48 (s, 1H), 8.22 (d, J=2.0 Hz, 1H), 7.94 (dd, J=8.4, 2.1 Hz, 1H), 7.75-7.85 (m, 3H), 7.44, (d, J=8.6 Hz, 2H), 4.76 (s, 2H); MS: (CI): m/z 314 (M$^+$+1); Anal. Calcd for $C_{14}H_{10}Cl_3NO$: C, 53.45; H, 3.20; N, 4.45; Cl, 33.81. Found: C, 53.53; H, 3.15; N, 4.27; Cl, 34.04.

A suspension of Compound B4 (54.35 g, 123.60 mmol) in acetone (395.50 g) was stirred and heated to a temperature of from about 40° C. to about 45° C. to afford a slightly hazy solution which was filtered directly into a 2000 mL 4-neck Morton flask equipped with an overhead stirrer, thermocouple, heating mantle, reflux condenser, and an addition funnel. 4-DMATHP Compound B5 (15.64 g, 115.02 mmol) was added via the addition funnel to the stirred solution over a period of about 10 minutes. The reaction was heated during the addition such that the solution was maintained at a gentle reflux (a temperature of from about 55° C. to about 56° C.). After the addition was complete, the reaction suspension was maintained at reflux for about 6 hours. The compound of Formula (Ia) began to precipitate after a few minutes at reflux.

The reaction was monitored by HPLC and was complete when the amount of residual Compound B4 relative to the compound of Formula (Ia) was <5% by area.

Once the reaction was complete, the suspension was cooled in an ice-bath at a temperature of from about 0° C. to about 3° C. The suspension was settled for a few minutes and then filtered. The solids were washed twice with acetone (79.10 g each), air dried for several hours and then dried in a vacuum oven overnight at 95° C. with a slow $N_2$ stream. The compound of Formula (Ia) was isolated as a white solid (40.41 g, 91.06 mmol). $^1$H NMR (300 MHz, DMSO-$d_6$): δ 10.8 (s, 1H), 8.28 (d, J=2.0 Hz, 1H), 7.83-8.01 (m, 3H), 7.85 (d, J=8.4 Hz, 1H), 7.58, (d, J=8.6 Hz, 2H), 4.50 (s, 2H), 4.04-4.09 (m, 2H), 3.61 (br t, J=12 Hz, 1H), 3.34 (br t, J=10 Hz, 2H), 2.89 (s, 6H), 2.15-2.19 (m, 2H), 1.81-1.92 (m, 2H); MS: (CI): m/z 407 (M$^+$); Anal. Calcd for $C_{21}H_{25}Cl_3N_2O_2$: C, 56.83; H, 5.68; N, 6.31; Cl, 23.97. Found: C, 56.66; H, 5.53; N, 6.17; Cl, 23.89.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A process for preparing a quaternary chloride salt compound of Formula (I):

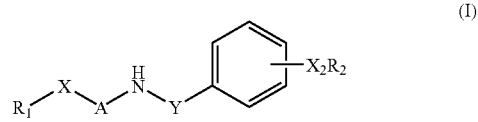

wherein

A is carbonyl;

X is a bond or —CH=CH—;

$R_1$ is selected from aryl and $C_5$-$C_{15}$cycloalkyl, wherein said aryl is optionally substituted with one or more lower alkyl, —$(CH_2)_n$—$CF_3$, lower alkoxy, alkoxycarbonyl, cyano, halogen or phenyl optionally substituted by lower alkyl, —$(CH_2)_n$—$CF_3$, lower alkoxy, alkoxycarbonyl, cyano or halogen, wherein said $C_5$-$C_{15}$cycloalkyl is optionally substituted with one or more lower alkyl, —$(CH_2)_n$—$CF_3$, lower alkoxy, alkoxycarbonyl, cyano or halogen, and wherein n is 0, 1, 2, 3 or 4;

Y is a bond or —$CH_2$—;

$X_2$ is —$(CH_2)_m$—, wherein m is 1 or 2;

$R_2$ is —$N^+(R_4R_5)$—$ZR_3$;

Z is —$(CH_2)_p$— wherein p is 0, 1 or 2;

$R_3$ is selected from aryl and $C_5$-$C_{15}$cycloalkyl wherein said aryl is optionally substituted with one or more lower alkyl, —$(CH_2)_n$—$CF_3$, lower alkoxy, aryl, halogen-substituted aryl, alkoxycarbonyl, cyano or halogen, wherein said $C_5$-$C_{15}$cycloalkyl is optionally substituted with one or more lower alkyl, —$(CH_2)_n$—$CF_3$, lower alkoxy, aryl, halogen-substituted aryl, alkoxycarbonyl, cyano or halogen, or and $R_4$ and $R_5$ are each individually lower alkyl or lower alkenyl;

comprising the steps of:

Step A. reacting a Compound A1 with a Compound A2, optionally in the presence of an aqueous base, to provide a Compound A3:

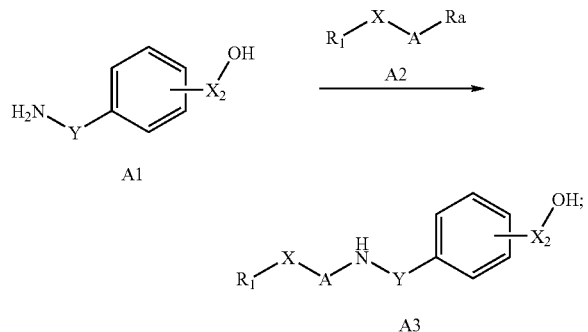

Ra is chloro;

Step B. reacting Compound A3 in the presence of an acid to provide a Compound A4:

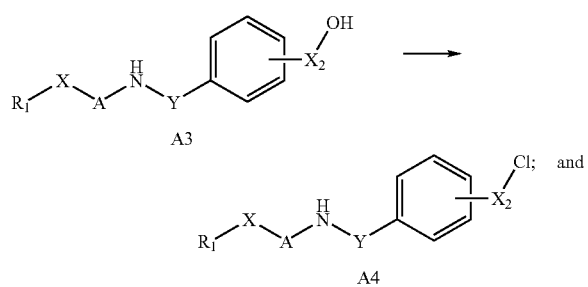

Step C. reacting Compound A4 with a Compound A5 in a solvent to provide Compound A6, representative of the compound of Formula (I):

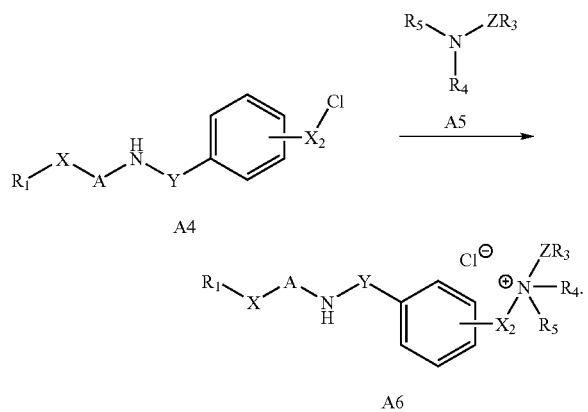

2. The process of claim 1, wherein the optional aqueous base is $Na_2CO_3$ (at a concentration of about 7.2%) and Compound A1 is reacted with Compound A2 in acetone at a reaction temperature in a range of from about 35 °C. to about 42 °C.

3. The process of claim 1, wherein Compound A1 is reacted with Compound A2 in the presence of $Na_2CO_3$ (at a concentration of about 7.2%) in acetone at a reaction temperature in a range of from about 35 °C. to about 42 °C.

4. The process of claim 1, wherein Compound A3 is reacted in the presence of an acid in a ratio with a solvent selected from the group consisting of THF, EtOH and acetone at a reaction temperature in a range of from about room temperature to about 45 °C.

5. The process of claim 4, where the acid is concentrated HCl and wherein the ratio of THF:HCl is about 1:1 at a reaction temperature of about room temperature.

6. The process of claim 4, wherein the acid is concentrated HCl and the ratio of EtOH:conc. HCl is about 1:1 at a reaction temperature of about room temperature.

7. The process of claim 4, wherein the acid is concentrated HCl and the ratio of acetone:HCl is about 1:1, or about 3:1, or about 4:1, or about 5.4:1, or about 6:1, or about 7.7:1, or about 12.8:1 at a reaction temperature of about RT, or about 30 °C., or about 35 °C., or about 40 °C., or about 45 °C.

8. The process of claim 1, wherein the acid may be an inorganic acid chloride selected from $SOCl_2$/THF and $SOCl_2$/$CHCl_3$/Pyridine(cat.).

9. The process of claim 1, wherein Compound A3 is reacted in the presence of concentrated HCl in a 3:1 ratio with acetone at a reaction temperature in a range of from about 45 °C. to about 50 °C.

10. The process of claim 1, wherein Compound A4 is reacted with a Compound A5 in a solvent selected from acetone and EtOH at a reflux temperature that is less than or about the boiling point of the solvent.

11. The process of claim 10, wherein Compound A5 is 4-DMATHP and is reacted with Compound A4 in acetone at said reflux temperature.

12. The process of claim 1, wherein the compound of Formula (I) is selected from the group consisting of:
(E)-(4-{[3-(3-bromo-phenyl)-acryloylamino]-methyl}-benzyl)-cyclohexyl-dimethyl-ammonium chloride,
{4-[(3 -bromo-benzoylamino)-methyl]-benzyl}-cyclohexyl-dimethyl-ammonium, chloride
cyclohexyl-dimethyl-{4-[(3-trifluoromethyl-benzoylamino)-methyl]-benzyl}-ammonium chloride,
bicyclo[2.2.1]hept-2-yl-[4-(3,4-dichloro-benzoylamino)-benzyl]-dimethyl-ammonium chloride,
cycloheptyl-[4-(3,4-dichloro-benzoylamino)-benzyl]-dimethyl-ammonium chloride,
(E)-cyclohexyl-{4-[3-(3,4-dichloro-phenyl)-acryloylamino]-benzyl}-dimethyl-ammonium chloride,
(E)-{4-[3 -(3 -bromo-phenyl)-acryloylamino]-benzyl}-cyclohexyl-dimethyl-ammonium chloride,
[4-(3-bromo-benzoylamino)-benzyl]-cyclohexyl-dimethyl-ammonium chloride,
cyclohexyl-dimethyl-[4-(3-trifluoromethyl-benzoylamino)-benzyl]-ammonium chloride,
cyclohexyl-[4-(3,4-dichloro-benzoylamino)-benzyl]-dimethyl-ammonium chloride,
[4-(3-chloro-4-fluoro-benzoylamino)-benzyl]-cyclohexyl-dimethyl-ammonium chloride,
cyclohexyl-[4-(2,3-dichloro-benzoylamino)-benzyl]-dimethyl-ammonium chloride,
cyclohexyl-[4-(2,6-dichloro-benzoylamino)-benzy]-dimethyl-ammonium chloride,
[4-(3 -chloro-4-methoxy-benzoylamino)-benzyl]-cyclohexyl-dimethyl-ammonium chloride,
[4-(3-chloro-4-methyl-benzoylamino)-benzyl]-cyclohexyl-dimethyl-ammonium chloride, cyclohexyl-[4-(2,5-dichloro-benzoylamino)-benzyl]-dimethyl-ammonium chloride,
cyclopentyl-[4-(3,4-dichloro-benzoylamino)-benzyl]-dimethyl-ammonium chloride,
(E)-cyclohexyl-{3-[3-(3,4-dichloro-phenyl)-acryloylamino]-benzyl}-dimethyl-ammonium chloride,
(E)-cyclohexyl-{3-[3-(4-fluoro-phenyl)-acryloylamino]-benzyl}-dimethyl-ammonium chloride,
cyclohexyl-dimethyl-{4-[(4'-methyl-biphenyl-3-carbonyl)-amino]-benzyl}-ammonium chloride, {4-[(7-bromo-naphthalene-2-carbonyl)-amino]-benzyl}-cyclohexyl-dimethyl-ammonium chloride,
{4-[(3-bromo-8,9-dihydro-7H-benzocycloheptene-6-carbonyl)-amino]-benzyl}-cyclohexyl-dimethyl-ammonium chloride, and
cyclohexyl-{4-[(8,9-dihydro-7H-benzocycloheptene-6-carbonyl)-amino]-benzyl}-dimethyl-ammonium chloride.

13. The process of claim 1 wherein the acid is neat concentrated HCl or concentrated HCl.

14. A compound selected from the group consisting of:
3,4-dichloro-N-(4-hydroxymethyl-phenyl)-benzamide, and
3,4-dichloro-N-(4-chloromethyl-phenyl)-benzamide.

* * * * *